US009265505B2

(12) United States Patent
Jones et al.

(10) Patent No.: US 9,265,505 B2
(45) Date of Patent: Feb. 23, 2016

(54) ENDOLUMINAL SURGICAL DELIVERY SYSTEM

(75) Inventors: Anthony Jones, Didcot (GB); Duncan Keeble, Didcot (GB)

(73) Assignee: Anson Medical Limited (GB)

( * ) Notice: Subject to any disclaimer, the term of this patent is extended or adjusted under 35 U.S.C. 154(b) by 1685 days.

(21) Appl. No.: 10/597,771

(22) PCT Filed: Feb. 9, 2005

(86) PCT No.: PCT/GB2005/000437
§ 371 (c)(1),
(2), (4) Date: Aug. 7, 2006

(87) PCT Pub. No.: WO2005/077280
PCT Pub. Date: Aug. 25, 2005

(65) Prior Publication Data
US 2007/0162053 A1 Jul. 12, 2007

(30) Foreign Application Priority Data
Feb. 9, 2004 (GB) .................................. 0402796.7

(51) Int. Cl.
| | | |
|---|---|---|
| A61B 17/10 | (2006.01) | |
| A61B 17/128 | (2006.01) | |
| A61B 17/12 | (2006.01) | |
| A61B 17/00 | (2006.01) | |
| A61B 17/64 | (2006.01) | |
| A61B 17/11 | (2006.01) | |
| A61F 2/958 | (2013.01) | |

(52) U.S. Cl.
CPC ......... *A61B 17/1285* (2013.01); *A61B 17/1204* (2013.01); *A61B 17/12036* (2013.01); *A61B 17/12136* (2013.01); *A61B 17/00234* (2013.01); *A61B 17/64* (2013.01); *A61B 2017/00535* (2013.01); *A61B 2017/1107* (2013.01); *A61B 2017/1205* (2013.01); *A61F 2/958* (2013.01)

(58) Field of Classification Search
CPC .................... A61B 17/115; A61B 2017/1135; A61B 2017/1107
USPC .................................. 604/528; 606/151, 142
See application file for complete search history.

(56) References Cited

U.S. PATENT DOCUMENTS

| | | | | | |
|---|---|---|---|---|---|
| 4,245,624 | A | * | 1/1981 | Komiya ........................ 600/106 |
| 4,758,221 | A | * | 7/1988 | Jureidini ................... 604/95.04 |
| 4,759,748 | A | * | 7/1988 | Reed .......................... 604/95.04 |
| 5,462,527 | A | * | 10/1995 | Stevens-Wright et al. ... 604/528 |

(Continued)

FOREIGN PATENT DOCUMENTS

| | | |
|---|---|---|
| JP | 2001-509398 A | 7/2001 |
| JP | 2001-314514 A | 11/2001 |

(Continued)

*Primary Examiner* — Gregory Anderson
*Assistant Examiner* — Christina Lauer
(74) *Attorney, Agent, or Firm* — Craig A. Fieschko, Esq.; DeWitt Ross & Stevens S.C.

(57) ABSTRACT

A system (1) for delivering a staple (9) to the locus of an artery (2) comprises a delivery conduit (5) for inserting into the lumen of an artery through which conduit a staple can be delivered to the locus, and an elongate element (6) such as a catheter for a balloon (7) for translating axial advancement of the delivery conduit through the artery into movement of the distal end of the delivery conduit away from the longitudinal axis of the artery and towards the artery wall.

25 Claims, 3 Drawing Sheets

(56) References Cited

U.S. PATENT DOCUMENTS

| | | | |
|---|---|---|---|
| 5,957,863 A | 9/1999 | Koblish et al. | |
| 5,997,556 A | 12/1999 | Tanner | |
| 6,126,633 A * | 10/2000 | Kaji et al. | 604/95.04 |
| 6,248,118 B1 | 6/2001 | Tanner et al. | |
| 6,270,516 B1 | 8/2001 | Tanner et al. | |
| 6,283,960 B1 | 9/2001 | Ashley | |
| 6,334,867 B1 | 1/2002 | Anson | |
| 6,416,522 B1 * | 7/2002 | Strecker | 606/143 |
| 6,419,686 B1 | 7/2002 | McLeod et al. | |
| 6,432,134 B1 | 8/2002 | Anson et al. | |
| 6,544,253 B1 * | 4/2003 | Tanner | 623/1.23 |
| 6,602,286 B1 | 8/2003 | Strecker | |
| 6,706,064 B1 | 3/2004 | Anson | |
| 6,814,747 B2 | 11/2004 | Anson et al. | |
| 6,899,728 B1 | 5/2005 | Phillips et al. | |
| 7,073,456 B2 | 7/2006 | Phillips et al. | |
| 2003/0033006 A1 | 2/2003 | Phillips et al. | |
| 2003/0120289 A1 * | 6/2003 | McGuckin et al. | 606/151 |
| 2003/0176766 A1 * | 9/2003 | Long et al. | 600/106 |
| 2003/0208232 A1 * | 11/2003 | Blaeser et al. | 606/213 |
| 2004/0116949 A1 * | 6/2004 | Ewers et al. | 606/167 |
| 2004/0138525 A1 * | 7/2004 | Saadat et al. | 600/104 |
| 2004/0176784 A1 * | 9/2004 | Okada | 606/142 |
| 2005/0154401 A1 * | 7/2005 | Weldon et al. | 606/139 |
| 2005/0251160 A1 * | 11/2005 | Saadat et al. | 606/153 |
| 2006/0149351 A1 | 7/2006 | Smirthwaite et al. | |

FOREIGN PATENT DOCUMENTS

| | | |
|---|---|---|
| WO | WO 99/00055 A2 | 1/1999 |
| WO | WO 99/04724 A | 2/1999 |
| WO | WO 00/07506 A | 2/2000 |
| WO | WO 00/16701 A | 3/2000 |
| WO | WO 01/58363 A | 8/2001 |

* cited by examiner

ENDOLUMINAL SURGICAL DELIVERY SYSTEM

FIELD OF THE INVENTION

The present invention relates to a system and method for delivering to the locus of an artery small surgical implants (such as staples) that are positioned intra-murally or trans-murally. Other applications of the system include the delivery of a temporary or permanent implant within a vessel but at a controlled and significant distance from the central axis of that vessel.

BACKGROUND OF THE INVENTION

Examples of vascular devices that can be delivered by the system are fixation staples or clips, occlusion coils, anasta-mosis devices and stents which are to be at least partially passed through the walls of a previously implanted graft. The delivery system enables staples, clips or other fixation devices to be passed from within the lumen of a vessel, through the wall of a graft or stent-graft and at least partially through the wall of the vessel, thereby attaching the graft or stent-graft to the vessel wall.

Endoluminal surgery is a rapidly expanding field and permits implants to be delivered and minor surgical procedures to be carried out within the lumen of vessels, most commonly in arteries. The main instruments used in the technique to traverse the arterial tree, from a puncture site in the skin to the destination site of the procedure, are guide wires, which pass through the vessel, and catheters, which are passed over the guide wires. By appropriate choice of combinations of guide wire and catheter, the system can be advanced through the vascular tree to the desired delivery site. Frequently, a stent or stent-graft (which are essentially open cylindrical structures) are passed through the catheter from outside the patient to the delivery site and, when released, these stents or stent-grafts expand to lie coaxially with the native vessel, their walls lying in close contact with the walls of the vessel.

Currently, it is very difficult to direct a guide wire or catheter into the wall of a vessel at a specific site because wires and catheters tend to lie approximately parallel to the axis of a vessel. Surgery will be eased by the ability to follow a guide wire along the axis of a vessel to a certain point and then to be able to move laterally away from the guide wire to deliver an implant in a position which is displaced from the wire, possibly in the wall of the vessel and not parallel to (and preferably at an angle approaching 90° to) the principal axis of the vessel.

U.S. Pat. No. 5,957,863 (Boston Scientific) and U.S. Pat. No. 6,283,960 (Oratec Interventions, Inc.) both disclose delivery systems in which a deflectable shaft/catheter is employed which may be deflected towards a vessel wall by pulling on a deflection wire attached to one side of the tip of the shaft/catheter. However, the relatively small radius of cross-section of the shaft/catheter tip results in a very small moment of deflection.

SUMMARY OF THE INVENTION

In accordance with a first aspect of the present invention, there is provided a system for delivering a staple to a locus of an artery, comprising a delivery conduit for inserting into the lumen of an artery through which conduit a staple can be delivered to the locus, and means for translating axial advancement of the delivery conduit through the artery into movement of the distal end of the delivery conduit away from the longitudinal axis of the artery and towards the artery wall.

The means for translating preferably comprises an elongate element for inserting into said artery and means for coupling the elongate element and the delivery conduit in situ, the elongate element being stiffer than at least the distal end of the delivery conduit The system may involve two guiding means, primary and secondary (corresponding to the elongate element and delivery conduit respectively). The primary guiding means may be a conventional guide wire and is introduced from outside the patient, through the patient's vessels to at least as far as the intended delivery site of the small implant. The secondary guiding means is able to follow the primary guiding means for at least part of the length of the primary guiding means. Said secondary guiding means is controlled by the practitioner so that at a point along the primary guiding means, the secondary guiding means can be wholly or partially separated from the primary guiding means and steered in a direction which is different from that of the primary guiding means.

Preferably, either one of the primary or the secondary guiding means is provided with a locking means which can be used to lock at least the secondary guiding means in place within the vessel to prevent both axial and lateral movement in that vessel. In the preferred embodiment, the locking means also prevents rotation of the secondary guiding means around the principal axis of the vessel.

The preferred embodiment of the secondary guiding means involves sets of components with two distinct functions. The first set of components controls the angle that the secondary guiding means makes with the wall of the vessel and preferably this is achieved by controlling the angle made by the secondary guiding means to the primary guiding means. Preferably, the angle which can be made between the secondary guiding means and the wall of the vessel can be controlled by the practitioner to be up to 90° and for the greatest range of uses, the angle made between the secondary and primary guiding means should be capable of being larger than 90°, i.e. the tip of the secondary guiding means can be angled to point backwards with respect to the tip of the primary guiding means. Useful functions can be achieved with less sophisticated embodiments if the angle is at least 45°, although some anatomies and some functions will not be accommodated with this restricted angle.

It is preferable that the angle made by the secondary guiding means to the wall of the vessel can be controlled and varied by the practitioner; however, simpler systems will operate with a fixed angle when the implant or surgical procedure can tolerate this limitation.

The second set of components of the secondary guiding means controls the distance of the tip of the secondary guiding means from the wall of the vessel and preferably this is achieved by controlling the distance of the tip of the secondary guiding means from the primary guiding means. For some applications, such as the delivery of staples, clips or pins through the wall of a graft or vessel, the tip of the secondary guiding means must be in contact with the vessel wall. In some cases, the tip must be able to apply significant pressure against the graft or vessel wall so that deployment of the staple, clip or pin does not push the wall away from the tip of the secondary guiding device. Thus the distance of the tip of the secondary guiding device from the vessel wall and the force which it applies to the vessel wall are to be controllable by the practitioner.

Such a system as described in general terms above is particularly difficult to design for larger vessels, such as the aorta, because the diameter of the vessel is such that a stiff guiding means is needed to traverse the width of the vessel and to provide support to deliver a trans-mural implant. However, stiffness of the guiding means must be sufficiently low to permit tracking through the vascular tree to the delivery site and it is difficult to achieve an appropriate degree of stiffness to meet these opposing requirements.

A particular use of such a delivery system is to allow an appropriately designed fixator pin or staple to be introduced through vessels along a guide wire and then, when the delivery site is reached, to divert the fixator or staple away from the guide wire and drive it through a graft to attach it to the wall of a vessel. This is of particular benefit in attaching stent-grafts to the walls of vessels in order to prevent or stop migration of the stent-graft.

Suitable staples are disclosed in WO 00/07506 and WO 01/58363 (both in the name of the present applicant), both of which are incorporated herein by reference in their entirety.

A simple method of constructing a delivery system with the properties described above is to combine at least one balloon, which is mounted on a catheter, with a separate delivery conduit. The balloon's catheter and the delivery conduit may be attached to each other for at least part of their length and in one embodiment, these two components can be constructed from a single tubular component with two lumens. In this case, the two lumens are preferably linked by a thin, flexible plastic web which can easily be divided.

In an alternative embodiment of the invention, the balloon's catheter and the delivery tube are separate parts which are joined at a single point close to the tip of the delivery tube. The attachment means used to make the said join allows the axis of the end of the delivery tube to make a changeable angle with respect to the axis of the catheter, while preventing the delivery tube from sliding up and down with respect to the catheter.

Typically, the balloon's catheter is manufactured from an extruded plastic material with an internal diameter sufficient to permit standard guide wires to pass through. In aortic surgery, the diameter of guide wires most commonly used is 0.035" and occasionally 0.038" although in other surgical sites, wires as small as 0.014" are used. By designing the balloon's catheter to be able to run over a previously introduced guide wire, the balloon's catheter comprises the primary guiding means described above. Preferably, the balloon's catheter is extruded with at least two lumens where the first lumen is used to pass over the guide wire and the second lumen transmits fluid used to inflate the balloon.

In some applications, it is preferable to include a metallic or similar stiff braid into the structure of the walls of the balloon's catheter in order to improve the transmission of torque from the practitioner, through the catheter, to the tip of the device. Typical external diameters of the balloon's catheter for use in the aorta will lie in the range 1.5 mm to 3.0 mm, although this size range will be scaled down for smaller vessels and smaller guide wires.

The construction of endovascular balloons is well known in the art. The balloon used in the preferred embodiment should be relatively compliant and operated at low pressures. Compliant balloons are typically manufactured from rubber, such as latex rubber or from elastic polymers such as polyurethane. Such balloons are typically inflated to pressures of approximately 2 atmospheres, although 5 atmospheres is used in some, less compliant balloons. High pressure balloons such as those manufactured from polyester or Mylar film are usually operated at pressures of several tens of atmospheres in order to dilate stenoses. Such balloons and pressures can be used in this device but are less effective unless the size of the balloon matches closely the size of the vessel in which it is placed.

Preferably, the balloon is designed so that it does not entirely occlude the vessel but provides some passage for blood to flow through or past it. This can be achieved by using more than one balloon, typically three balloons, located at the same axial point on the balloon's catheter and distributed around the catheter. When inflated the three balloons swell to form a 'clover leaf' shape which allows blood to flow through the spaces between the lobes and past the balloon.

Alternatively, single balloons can be constructed with fenestrations. In the simplest case, an annular balloon (resembling a doughnut) is inflated with the balloon's catheter filling the balloon by an attachment point on the surface of the inner ring of the doughnut. In this case, the catheter is slightly offset from the mid-line of the balloon. When inflated, the central fenestration of the balloon will provide a convenient channel for the through-flow of blood. If the balloon is designed not to be axi-symmetric, the balloon's catheter can be arranged to lie on the axis of the vessel but the balloons' fenestrations must then be offset.

Alternative locking mechanisms to balloons can be constructed from strips of suitably springy material such as wire or strip metal which are arranged to 'balloon' out. Such an arrangement is constructed by distributing at least two approximately equal length wires or strips uniformly around a central shaft and attaching the ends of the strips to collars or similar structures which can slide over the shaft. When the collars are pushed or pulled together by appropriate means, the wires or strips will 'balloon' out from the shaft to lock across the width of the vessel. A suitable system is disclosed in WO 00/07506.

Other versions of the concept are also possible in which stiffer strips or wires are employed with hinges placed at points encountering large strains when the locking device is expanded, such as at the collars and in the mid part of the strips or wires. An attractive manufacturing technique for such a construct is to use injection moulding to form the strips from plastic, the hinges being constructed from sections of the same plastic where the thickness has been greatly reduced (so called 'living hinges').

Typically the delivery tube also comprises an extruded plastic conduit. Preferably at least the inner surface of the tube is treated to have a low sliding friction, either by means of a lubricant, such as a silicon-based grease or oil, or by extruding or coating at least the luminal part of the tube from a hard or low friction plastic such as PTFE.

In some applications, it is preferable to include a metallic or other similar braid into the structure of the walls of the delivery tube in order to improve the transmission of torque from the practitioner, through the tube, to the tip of the device.

In some embodiments of the device, the properties of the delivery tube will preferably vary along the length of the tube. At the tip of the tube, the last few centimeters can benefit if made to be less flexible than the rest of the tube and preferably a pre-set bend is formed in this stiffer region so as to direct the tube away from the balloon's catheter. In this way, the tube comprises the first part of the secondary guiding means.

Other variations can be devised for instance to allow the tube to penetrate some distance down small, side-branch vessels. In this case, it may be advantageous for the last few centimeters of the tip of the tube to be flexible so that it can track down the side branch. A stiffer, pre-curved section would then be position just behind this deformable tip so as to direct the tip away from the balloon's catheter.

In a further variation of the tube, at least one stay or tensioning element manufactured from a filamentous material such as a braided or monofilament surgical suture or wire is attached close to the tip of the tube and is preferably fed through at least one additional lumen for at least part of the length of the tube. When tension is applied to at least one of the stays or tensioning elements in such a way that more tension is applied to one side of the tube than another, then the tube will bend in the direction of the greatest tension.

In the simplest embodiment of this variation, a single stay is connected close to the tip of the tube and runs back from the tip for a distance of between 2 cm and 10 cm, at which distance it passes through a small hole in the wall of the tube and continues to run back for the whole of the rest of the length of the tube inside the tube, preferably within its own lumen. Where the tube exits the patient's body, the stay is attached to some independent gripping means. When the practitioner pulls on the independent gripping means and applies tension to the stay, while at the same time holding the tube to prevent the stay from pulling it out of the patient, the tip of the tube will bend in response to the tension in the stay.

The attachment means between the tube and the catheter's balloon can be constructed with a variety of methods. The simplest is to employ a small lashing with a thread-like material such as monofilament or multifilament surgical suture or yarn.

Preferably, the suture or yarn is passed around the tube and the balloon's catheter in a 'figure of eight' form so as to provide a point of rotation between the two and to limit the relative axial movement between the tube and the catheter. Similar structures can be constructed from moulded loops of preferably elastomeric or plastic material or from moulded 'figures of eight' from similar materials. In order to prevent axial relative motion between the tube and the catheter, indents or protrusions can be incorporated into the surface of the catheter or the tube or both conduits. Alternatively, where the tube and catheter are formed from a single extrusion, a section of the tube part can be separated from its adjoining section of the catheter part as a manufacturing step. A short section, typically between 1 and 5 mm long, where the attachment between the tube and catheter has not been separated, located towards the tip of the tube will also provide a suitable degree of flexion between the tube and catheter. In some embodiments, it will be possible to retain attachments of both lumens for the majority of their lengths, separation only being required at a point where the balloon can be inserted between the tube and catheter.

Preferably, where there is a single balloon, fenestrated balloon or group of lobular balloons, the tube is arranged to run past the outside of the balloon and to curve away from the balloon's catheter once it has passed the balloon. In another embodiment of the device, a second balloon, fenestrated balloon or group of lobular balloons is arranged at a second point along the length of the balloons catheter. Preferably, the tube is arranged to run past the first balloon or group of balloons and to bend away from the balloon's catheter before reaching the second balloon or group of balloons which are located further along the balloon's catheter.

In all arrangements here described, the first function of the first balloon or group of balloons is to fix the balloon's catheter in the vessel to prevent it from moving axially, laterally or from rotating.

A second function of the first balloon is to permit the tube to form its curve away from the balloon's catheter using the full diameter of the vessel. This allows the radius of the bend of the tip of the tube to be greater which permits it to be manufactured from stiffer material and which permits longer or stiffer implants or devices to be passed therethrough. Were the tube to bend away directly from the balloon's catheter towards the wall of the vessel without first reaching the opposite wall of the vessel, the bend of the tube would have to be completed within just the radius of the vessel requiring the tip of the tube to be more flexible and restricting the stiffness or length of implants or devices past through the tube.

A third function of the first balloon is to deflect the tube so that it bends away from the balloon's catheter and is pushed against the wall of the vessel, locking it in place. In use, the position at which the sheath is pressed by the balloon against the vessel wall is approximately opposite the part of the wall where the tip of the secondary guidance means is intended to contact.

A fourth function of the first balloon is to support the tube at approximately the midpoint of its traverse from one wall to the opposite wall of the vessel. Where this is a significant distance, such as in the aorta, the tube can lack the stiffness required to deliver a staple or fixation device successfully. Attachment of the tube at this said approximate midpoint approximately halves the unsupported length of the tube and greatly increases the stability of this part of the delivery system.

Where two balloons or groups of balloons are employed, the function of the second balloons or group of balloons is both to provide supplementary fixation and also to occlude or reduce the flow of blood. This is because in some applications, such as stapling at the neck of an aortic aneurysm, the first balloon may be situated within part of a stent-graft that is not well fixed to the walls of the vessel. In this case, inflation of a single balloon and the subsequent force of blood upon it may cause the balloon to dislodge the stent-graft, causing it to migrate before a fixation device has been deployed. In this type of case, the second balloon can be inflated upstream of the first balloon in a region of the vessel where there is no stent-graft or where the second balloon will be firmly fixed against the wall of the vessel. Once inflated, the second balloon will reduce or occlude the pressure of blood striking the first balloon, reducing or removing the risk of it migrating and causing an unwanted migration of a stent-graft or other such structure.

Preferably the first balloon or group of balloons can be inflated independently of the second balloon or group of balloons, for example by the use of separate inflation lumens in the balloon's catheter.

Typically the delivery tube will have an internal diameter between 1 mm and 7 mm depending upon the application.

Some benefits may accrue if more than one inner tube is deployed around the delivery tube as this permits the simultaneous or near-simultaneous deployment of more than one implant or device at different points around the circumference of the vessel. Such a modification to the design at its simplest involves the duplication of the tube components.

In accordance with a second aspect of the present invention, there is provided a method for delivering a staple to a locus of an artery, comprising carrying out the following the steps in any convenient order:

(i) loading a staple into a delivery conduit,
(ii) inserting the conduit into the lumen of an artery, together with means for translating axial advancement of the delivery conduit through the artery into movement of the distal end of the delivery conduit away from the longitudinal axis of the artery and towards the artery wall,
(iii) positioning the distal end of the conduit near the locus,
(iv) advancing the conduit through the artery relative to said means for translating movement in order to move the distal end of the conduit away from the longitudinal axis of the artery and towards the artery wall, and (v) ejecting the staple from the conduit at the locus.

In the simplest embodiment, a delivery catheter is passed through the tube. At the tip of the tube, which is arranged either by pre-curvature or by the action of the balloon or by both of these characteristics, to point away from the balloon's catheter, the delivery catheter can be advanced through the tip of the tube and towards its eventual target site. Thus the delivery tube can be pushed into contact with the wall of the vessel and can be made to exert a significant force against that wall. In some embodiments, the tip of the delivery catheter is also curved in order that it makes a greater angle with the axis of the balloon catheter.

In some applications, the delivery catheter is conveniently pre-loaded with a staple or other fixator. Preferably, the sheath is fitted with a haemostatic valve at the end which lies outside the patient and this permits the delivery catheter to be completely withdrawn from the delivery system after its staple of fixator contents have been deployed. Once removed, the delivery catheter can be replaced with a second delivery catheter, allowing a subsequent staple or fixator to be deployed without having to move the delivery system from the deployment site of the previous staple or fixator.

For the application of deploying staples disclosed in WO 01/58363 in the name of the present applicant in which the staples are biased to open outwards from an initial, approximately linear configuration, the diameter of the lumen of the delivery catheter will preferably lie in the range 2 mm±1 mm. These dimensions are appropriate for staples of the said design which have a deployed width lying in the range 10 mm to 15 mm. Other sizes of staple will require appropriate scaling of the diameter of the delivery catheter.

Preferably, an overall sheath is used to contain the balloon, balloon's catheter, the delivery tube and the delivery catheter. Preferably, the tip of the balloon's catheter is furnished with a tapered nose cone that will allow the overall sheath to pass through the vessels without damaging the vessel walls. The diameter of the overall sheath will lie in the range 8 to 30 French (2.6 mm to 10 mm) although currently constructed prototypes lie in the range 14 French to 20 French (4.6 mm to 6.6 mm). Slightly smaller systems can be designed with sheath sizes of 5 French but these systems involve the finest guide wires, dual or multiple purpose lumens and advanced materials. Preferably the overall sheath is constructed from a stiff plastic such as nylon or PTFE and itself is fitted with a haemostatic valve to prevent leakage of blood where the sheath and balloon's catheter exit from the back of the overall sheath.

Preferably, at least one of the sheath, the balloon's catheter and the delivery sheath are fitted with a suitable handle or gripping region to allow the practitioner to manipulate these conduits from outside the patient.

In use the following steps are used to deploy a staple such as that disclosed in WO 01/58363 (the contents of which are incorporated herein by reference):

A guide wire is introduced into the patient so that it lies in the vessel into whose wall the staple is to be delivered. The guide wire is preferably advanced several tens of centimeters beyond the delivery site.

The delivery site is identified, typically by means of fluouroscopy and radio-opaque dye.

The delivery system is fed onto the guide wire with the wire passing through the lumen of the balloon's catheter.

The delivery system is advanced through the patient until the end of the sheath is approximately opposite the intended delivery site of the staple.

Holding the delivery system still, the overall sheath is pulled back to release the balloon and sheath within the vessel.

The balloon and sheath are manipulated until the sheath is pointing at the correct part of the wall of the vessel.

The balloon is inflated.

The delivery catheter is advanced through the sheath until it is in near contact with the wall of the vessel.

Pressure in the balloon is slightly reduced to permit fine adjustment of the position of the tip of the delivery catheter.

When the tip of the delivery catheter is correctly aligned, the balloon is inflated up to its maximum recommended pressure.

The delivery catheter is pushed firmly against the wall of the vessel and the staple is deployed.

The delivery catheter is withdrawn, If necessary completely from the delivery system.

A new delivery catheter containing a new staple is pushed into the delivery system and advanced to the wall of the vessel.

The pressure in the balloon is dropped slightly and the tip of the delivery catheter is repositioned to the delivery site for the new staple.

The sequence is repeated.

BRIEF DESCRIPTION OF THE DRAWINGS

A number of preferred embodiments of the invention will now be described, with reference to the accompany drawings, in which.

DETAILED DESCRIPTION OF PREFERRED VERSIONS OF THE INVENTION

Figure 1:
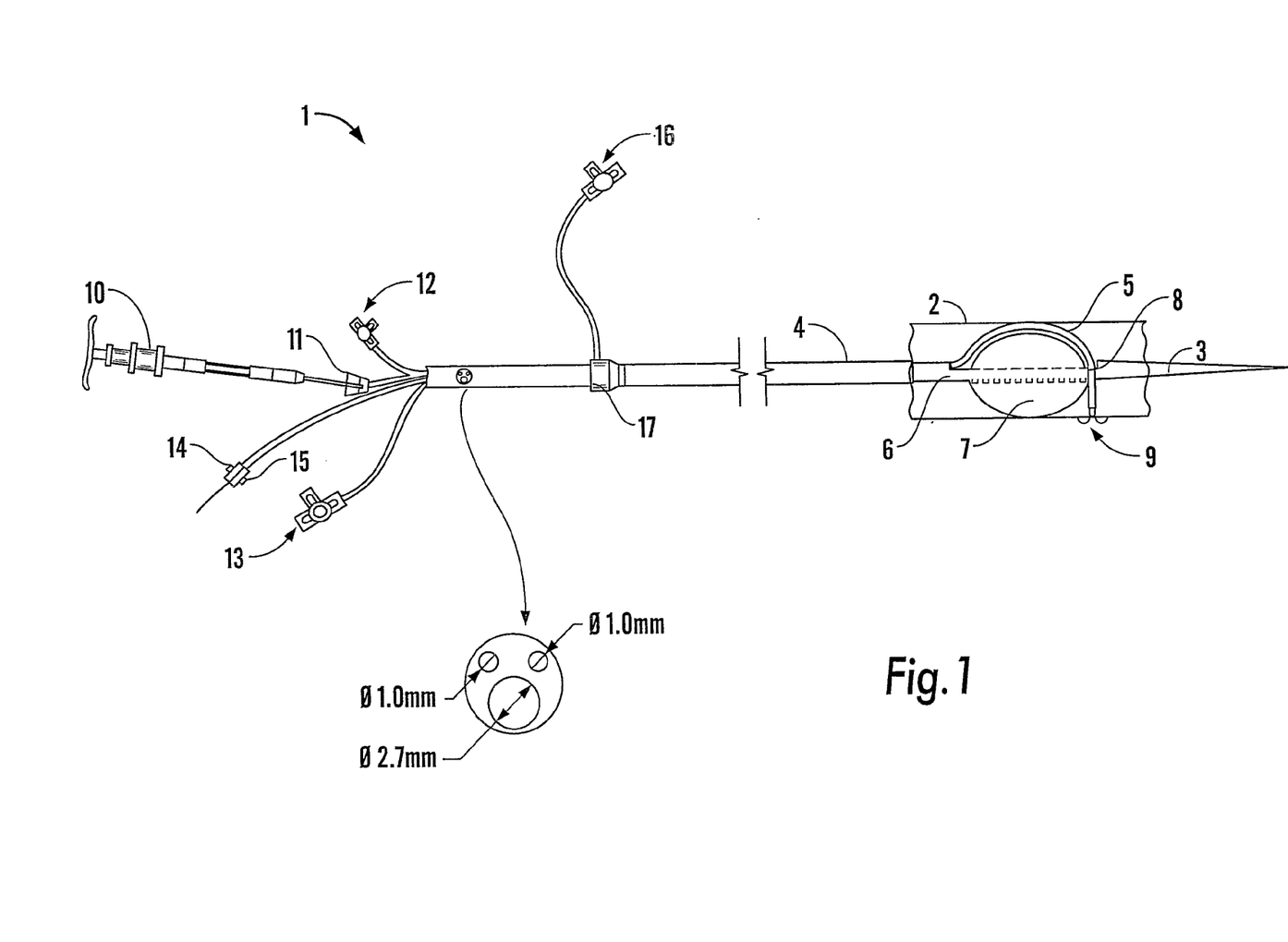
FIG. 1 shows a schematic overview of a system for delivering a staple in accordance with the invention.

Referring to FIG. 1, system 1 comprises sheath 4, which contains delivery tube 5 and balloon catheter 6 for balloon 7. The entire system is threaded in use over guide wire 3 (which resides inside balloon catheter 6) inside vessel 2 (which may be for example a human artery).

The distal end of delivery tube 5 is coupled to balloon catheter 6 by lashing 8, which will be described in more detail below in relation to FIGS. 4-8.

The tip of delivery tube 5 is flexible and radio-opaque so that it is visible to radio imaging equipment to enable the user of system 1 to "see" the end of delivery tube 5 in situ.

Delivery tube 5 is loaded with staples 9 by staple injector 10 which is mounted at the proximate end of system 1 to the user (the opposite end to the locus of vessel 2 to which staple 9 is delivered). Staple injector 10 is connected to the proximate end of delivery tube 5 via haemostatic valve 11, and slightly downstream of this is stapler flushing port 12. Staple injector 10 has a delivery sheath (not shown) which in use is threaded through delivery tube 5 to the distal end thereof for delivery of staples 9.

Proximate end of system 1 also has guide wire port 14, leur port 15, and balloon inflation port 13 for balloon catheter 6.

Flushing port 16 is in communication with sheath 4 via haemostatic sheath 17 as shown on FIG. 1. The effective length of the device from haemostatic sheath 17 to the distal end of balloon catheter 6 is about 750 mm. Balloon catheter 6 has an internal diameter of about 2.7 mm and delivery tube 5 an internal diameter of about 1.0 mm, resulting in an approximate total internal diameter of sheath 4 of about 4.4 mm.

In use, guide wire 3 is threaded through the vascular tree of the patient until it reaches the locus of the artery where it is intended to deliver a staple. The locus may for example be where a graft or stent-graft is in place which it is desired to attach to the artery wall. The delivery site is typically identified by means of fluoroscopy and radio-opaque dye.

Sheath 4 is then threaded over the part of guide wire 3 external to the patient's body (by means of balloon catheter 6) and sheath 4 is then carefully advanced over guide wire 3 down through the vascular tree until the distal end is approximately opposite the intended delivery site of the staple.

Whilst holding system 1 immobile, sheath 4 is retracted to release balloon catheter 6 and delivery tube 5 within vessel 2. These are then manipulated till the distal end of delivery tube 5 is pointing at the correct part of the wall of vessel 2.

Balloon inflation port 13 is then opened and filled with air to inflate balloon 7, thereby locking balloon catheter 6 in vessel 2 by contact of balloon 7 with its walls.

Advancement of delivery tube 5 through sheath 4 is resisted by lashing 8 which connects delivery tube 5 to balloon catheter 6. Further advancement of tube 5 therefore results in deflection of the distal end of tube 5 away from the longitudinal axis of vessel 2 and towards its wall at an angle approaching 90°.

Pressure in balloon 7 maybe slightly reduced putting a fine adjustment of the position of the tip of tube 5, following which balloon 7 can be fully inflated. Tube 5 is then pushed firmly against the wall of vessel 2 and staple 9 is deployed.

Once the staple has been deployed, delivery tube 5 can be withdrawn, if necessary completely, from system 1 and a new delivery tube containing a new staple can be inserted into system 1 and advanced to a new locus.

In an alternative embodiment, inflation of balloon 7 may cause delivery tube 5 to follow an arc around the perimeter of balloon 7, thereby angling distal end of delivery tube 5 approximately perpendicular with the walls of vessel 2.

Figure 2:
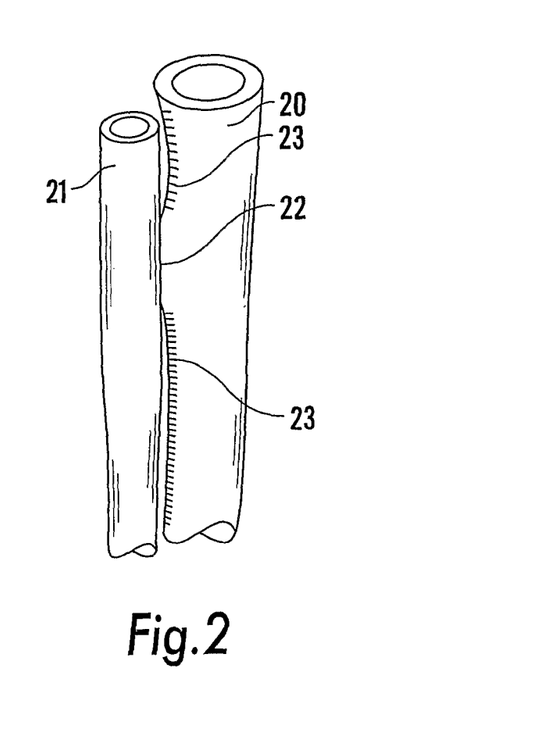
FIG. 2 shows a schematic illustration of an alternative embodiment of the invention.
Figure 3:
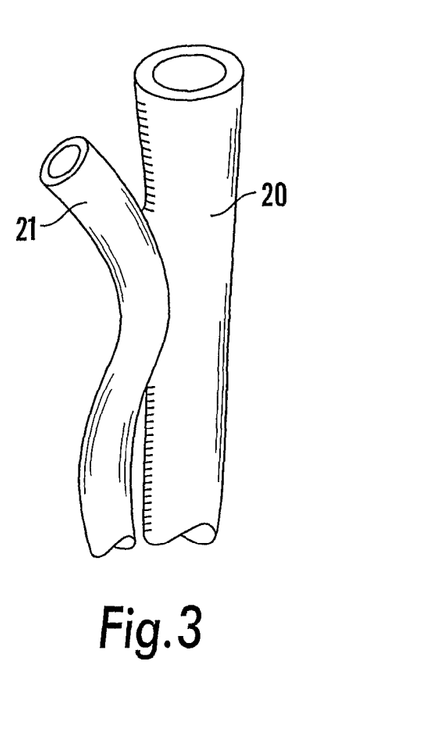
FIG. 3 is a schematic illustration of the embodiment of FIG. 2 in use.

As mentioned above, in one embodiment the present invention delivery tube 5 is attached to balloon catheter 6 by means of lashing 8. Referring to FIGS. 2 and 3, however, an alternative embodiment comprises balloon catheter 20 and delivery tube 21 which are formed from the same plastics material and are joined by a thin web. Web may then be removed along with the majority of the lumens (23) leaving join 22. In use, advancement of delivery tube 21 along the axis of an artery whilst balloon catheter 20 remains relatively immobile causes delivery tube 21 to bend towards the artery wall as shown schematically in FIG. 3.

Four alternative embodiments involve different ways of lashing a delivery tube to an elongate element (such as a balloon catheter) are shown in FIG. 4-8.

Figure 4:
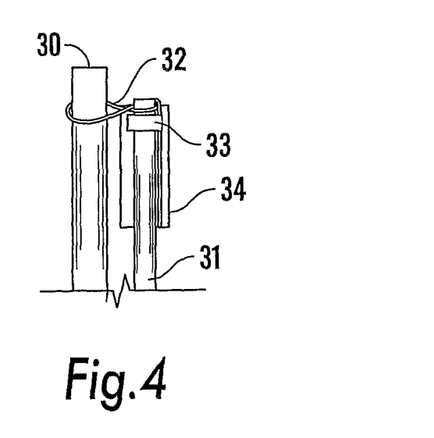
FIGS. 4-8 are schematic illustrations of further alternative embodiments of the invention.

FIG. 4 shows delivery tube 31 attached to catheter 30 by means of a suture 32 which is looped around catheter 30 and attached to tube 31 by means of crimp band 33 and heat-shrink sleeve 34.

Figure 5:
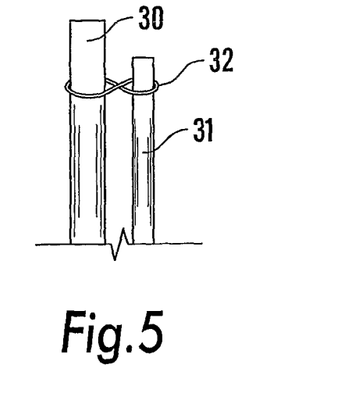

In FIG. 5, catheter 30 and delivery tube 31 are coupled by means of suture 32 which has been formed into a figure-of-eight and knotted.

Figure 6:
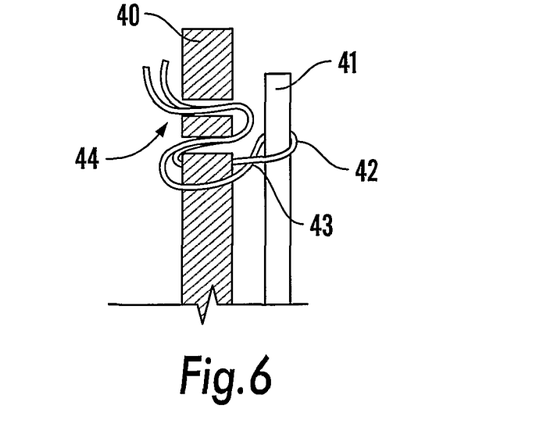

FIG. 6 shows an arrangement in which suture 42 is looped around delivery tube 41 and then threaded through fenestrations 44 in catheter 40 where it is bonded in place (for example with adhesive).

Figure 7:
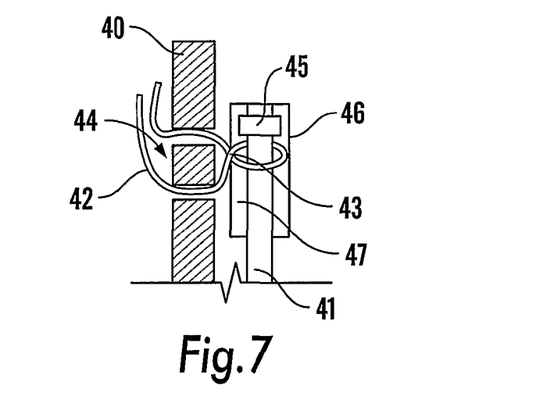
Figure 8:
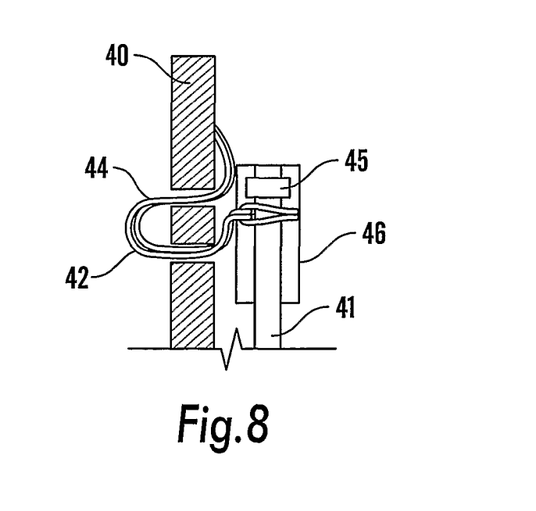

FIG. 7 shows an alternative arrangement also involving fenestrations 44 in catheter 40 in which a twist 43 is placed in suture 2 and delivery tube 41 passed through the resultant loop. The loop is then attached to tube 41 by means of a heat-shrink sleeve 46 having a hole 47 therein. Radio-opaque marker band 45 is employed at the distal end of tube 41. FIG. 8 shows a completed view of the attachment means of FIG. 7.

The invention claimed is:

1. A system for delivering a staple to a locus of an artery comprising
    a. a delivery conduit insertable within the lumen of an artery, through which delivery conduit a staple can be delivered to the locus, wherein the delivery conduit has a distal end flexibly connected to a proximal section of the delivery conduit, whereby the distal end of the delivery conduit may be oriented at an angle with respect to the proximal section of the delivery conduit;
    b. an elongated insertion element insertable within the lumen of an artery alongside the delivery conduit, the insertion element:
        (1) having an at least substantially inexpandable diameter, and
        (2) having an insertion element joinder location pivotally coupled to the delivery conduit at a delivery conduit joinder location at or adjacent the distal end of the delivery conduit, the pivotal coupling:
            (a) fixing the insertion element joinder location and the delivery conduit joinder location at an at least substantially constant distance between each other, and
            (b) being defined by a flexible tether extending between the insertion element joinder location and the delivery conduit joinder location, the flexible tether extending about and/or into one or both of the insertion element and the delivery conduit,
    wherein:
    i. the insertion element has an outer circumference extending alongside and exterior to an outer circumference of the delivery conduit at the pivotal coupling, and for lengths extending proximally and distally therefrom, and
    ii. the outer circumference of the delivery conduit extends alongside and exterior to the outer circumference of the insertion element at the pivotal coupling;
    whereby advancing the proximal section of the delivery conduit toward the distal end of the delivery conduit causes bending of the delivery conduit such that the angle of the distal end of the delivery conduit changes.

2. The system of claim 1 wherein the insertion element is defined by:
    a. a guide wire, or
    b. a catheter through which a guide wire extends.

3. The system of claim 1 wherein the insertion element includes an inflatable balloon thereon.

4. The system of claim 3 wherein the inflatable balloon is situated between the insertion element and the delivery conduit.

5. The system of claim 4 wherein the distal end of the delivery conduit is situated closer to the insertion element than the balloon when the balloon is inflated.

6. The system of claim 4 wherein:
    a. the insertion element has:
        (1) a balloon side, the balloon side being adjacent the balloon, and
        (2) a stapling side,
        along the length of the insertion element;

b. the distal end of the delivery conduit is axially directed toward the stapling side when the balloon is inflated.

7. The system of claim 1 wherein:
a. the insertion element is a catheter mounted on a guide wire, and
b. the insertion element bears an inflatable balloon.

8. The system of claim 1 wherein a distal end of the insertion element extends longitudinally beyond the distal end of the delivery conduit.

9. A system for delivering a staple to a locus of an artery, the system including:
a. a delivery conduit insertable within the lumen of an artery, wherein the delivery conduit includes:
 (1) a proximal delivery conduit section,
 (2) a distal delivery conduit section terminating in a distal delivery conduit end, the distal delivery conduit section being flexibly joined to the proximal delivery conduit section such that the distal delivery conduit end may be oriented at an angle with respect to the proximal delivery conduit section,
 (3) an outer delivery conduit surface extending along the proximal and distal delivery conduit sections, and
 (4) an inner passage through which a staple can be delivered to the locus;
b. an elongated insertion element having an outer insertion element surface extending alongside the outer delivery conduit surface and being joined thereto at a joinder location at or adjacent the distal end of the delivery conduit, with:
 (1) the outer insertion element surface and the outer delivery conduit surface being pivotally fixed together by a flexible filament at the joinder location, and
 (2) a distal end of the elongated insertion element:
  (a) extending longitudinally beyond the distal end of the delivery conduit, and
  (b) having an at least substantially inexpandable diameter,
 whereby advancing the proximal section of the delivery conduit toward the distal end of the delivery conduit causes bending of the delivery conduit such that the angle of the distal end of the delivery conduit changes.

10. The system of claim 9 wherein the flexible filament extends about and/or into one or both of the insertion element and the delivery conduit.

11. The system of claim 9 wherein the delivery conduit and insertion element extend alongside and exterior to each other at the joinder location, and for a length extending proximally thereto.

12. The system of claim 9 wherein the insertion element is defined by:
a. a guide wire, or
b. a catheter through which a guide wire extends.

13. The system of claim 9 wherein the insertion element includes an inflatable balloon thereon.

14. The system of claim 13 wherein the inflatable balloon is situated between the insertion element and the delivery conduit.

15. The system of claim 14 wherein the distal end of the delivery conduit is situated closer to the insertion element than the balloon when the balloon is inflated.

16. The system of claim 14 wherein:
a. the insertion element has:
 (1) a balloon side, the balloon side being adjacent the balloon, and
 (2) a stapling side,
 along the length of the insertion element;

b. the distal end of the delivery conduit is axially directed toward the stapling side when the balloon is inflated.

17. The system of claim 9 wherein:
a. the insertion element is a catheter mounted on a guide wire, and
b. the insertion element bears an inflatable balloon.

18. A system for delivering a staple to a locus of an artery, the system including:
a. a delivery conduit insertable within the lumen of an artery, wherein the delivery conduit includes:
 (1) a proximal delivery conduit section,
 (2) a distal delivery conduit section terminating in a distal delivery conduit end, the distal delivery conduit section being flexibly joined to the proximal delivery conduit such that the distal delivery conduit end may be oriented at an angle with respect to the proximal delivery conduit section,
 (3) an outer delivery conduit surface extending along the proximal and distal delivery conduit sections, and
 (4) an inner passage through which a staple can be delivered to the locus;
b. an elongated insertion element having an outer insertion element surface extending alongside the outer delivery conduit surface and being joined thereto by a flexible tether at a joinder location at or adjacent the distal end of the delivery conduit, with:
 (1) the outer insertion element surface and the outer delivery conduit surface being pivotally fixed together at the joinder location, and
 (2) a distal end of the elongated insertion element:
  (a) extending longitudinally beyond the distal end of the delivery conduit, and
  (b) having an at least substantially inexpandable diameter,
wherein:
 i. the insertion element has an outer circumference extending alongside and exterior to an outer circumference of the delivery conduit at the pivotal coupling, and
 ii. the outer circumference of the delivery conduit extends alongside and exterior to the outer circumference of the insertion element at the pivotal coupling;
whereby advancing the proximal section of the delivery conduit toward the distal end of the delivery conduit causes bending of the delivery conduit such that the angle of the distal end of the delivery conduit changes.

19. The system of claim 18 wherein the flexible tether extends about and/or into one or both of the insertion element and the delivery conduit.

20. The system of claim 18 wherein the insertion element is defined by:
a. a guide wire, or
b. a catheter through which a guide wire extends.

21. The system of claim 18 wherein the insertion element includes an inflatable balloon thereon.

22. The system of claim 21 wherein the inflatable balloon is situated between the insertion element and the delivery conduit.

23. The system of claim 21 wherein the distal end of the delivery conduit is situated closer to the insertion element than the balloon when the balloon is inflated.

24. The system of claim 21 wherein:
a. the insertion element has:
 (1) a balloon side, the balloon side being adjacent the balloon, and
 (2) a stapling side,
 along the length of the insertion element;

b. the distal end of the delivery conduit is axially directed toward the stapling side when the balloon is inflated.

25. The system of claim 18 wherein:
a. the insertion element is a catheter mounted on a guide wire, and
b. the insertion element bears an inflatable balloon.

\* \* \* \* \*